United States Patent [19]
Thies

[11] 4,305,303
[45] Dec. 15, 1981

[54] SAMPLING DEVICE AND METHODS FOR COLLECTING A LIGHTER MEDIUM FLOATING ON A HEAVIER MEDIUM

[75] Inventor: Howard J. Thies, Houston, Tex.

[73] Assignee: Texaco Inc., White Plains, N.Y.

[21] Appl. No.: 122,218

[22] Filed: Feb. 19, 1980

[51] Int. Cl.³ .......................... G01N 1/00; G01N 1/18
[52] U.S. Cl. .................................. 73/863.21; 73/444; 422/101; 210/540
[58] Field of Search ................... 73/425.4 R, 61.1 R; 422/101; 210/540

[56] References Cited

U.S. PATENT DOCUMENTS

| | | |
|---|---|---|
| 0,766,205 | 8/1904 | Walter . |
| 3,464,258 | 9/1969 | Lerner ................................ 73/61.1 |
| 3,586,064 | 6/1971 | Brown et al. ...................... 210/540 |
| 3,870,639 | 3/1975 | Moore et al. ..................... 422/101 |
| 4,136,008 | 1/1979 | Pogonowski . |

FOREIGN PATENT DOCUMENTS 16697 of 1888 United Kingdom ................ 73/61.1

Primary Examiner—S. Clement Swisher
Attorney, Agent, or Firm—Carl G. Ries; Robert A. Kulason; Theron H. Nichols

[57] ABSTRACT

A method for collecting a small sample of a lighter medium floating on the surface of a heavier medium in an open topped container comprises lowering an elongated tube into the mediums for forcing the lighter medium up into the elongated tube for testing or the like. A lighter medium collection device for carrying out the above method and a method of assembling a sampling device are disclosed.

27 Claims, 1 Drawing Figure

U.S. Patent     Dec. 15, 1981     4,305,303
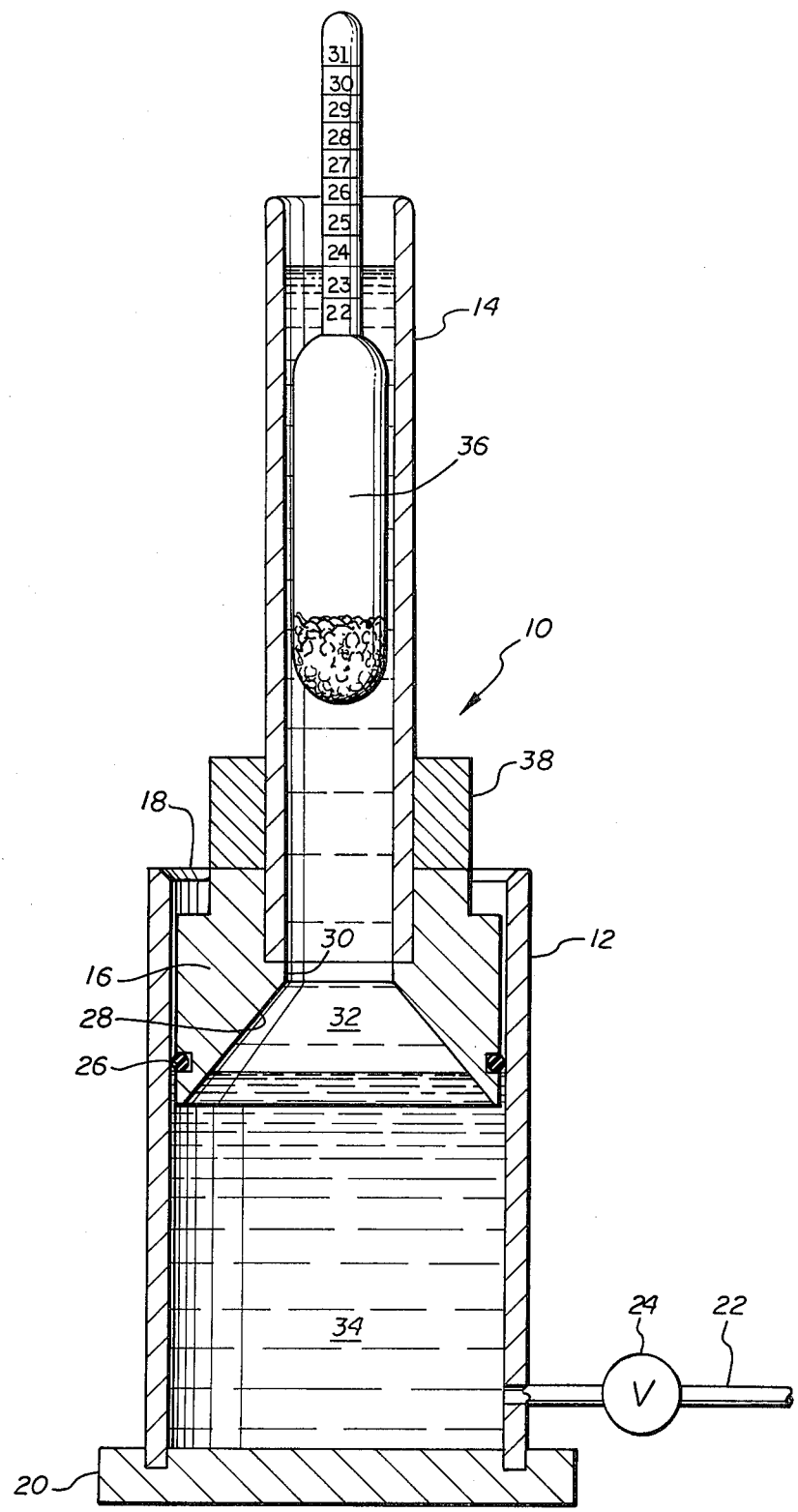

SAMPLING DEVICE AND METHODS FOR COLLECTING A LIGHTER MEDIUM FLOATING ON A HEAVIER MEDIUM

BACKGROUND OF THE INVENTION

Oil demulsifier testing requires the collection of a small oil sample, as 10 to 30 ml for example, from an oil layer for making a B.S.& W. (Basic Sediments and Water) test thereon. This small sample may be removed for further testing or a hydrometer, syringe, or the like may be inserted in the sample liquid for testing. The disclosed testing device and method are superior to others because only small samples of oil or emulsion in the field are usually required, thereby leaving little oil for discarding and thus the disposal problem is minimized greatly. This disposal problem has become quite critical due to the Government EPA (Environmental Protection Agency) now requiring great care be taken with all waste liquids.

In many oil fields an emulsion sample taken at the wellhead may consist of 95% water. To obtain a specific gravity reading of the oil in the emulsion, a large quantity of emulsion must be used. This method is wasteful and makes quite a disposal problem at the wellhead. However, with the disclosed sampler, only a small sample of emulsion is required for determination of the specific gravity of the oil in the emulsion. The determination is done faster than by the conventional method, waste emulsion is eliminated, and the disposal problem at the wellhead is eliminated.

OBJECTS OF THE INVENTION

Accordingly, a primary object of this invention is to provide a method for collecting a small sample of a lighter medium floating on a heavier medium for testing or the like.

Another primary object of this invention is to provide a sampling device for collecting a small sample of a lighter medium floating on a heavier medium for testing or the like.

A further primary object of this invention is to provide a method for forming and assembling a sampler for collecting a small sample of lighter medium floating on a heavier medium for testing or the like.

A further object of this invention is to provide a mechanism for carrying out the method for collecting a small sample of a lighter medium floating on a heavier medium that is easy to operate, is of simple configuration, is economical to build and assemble, and is of greater efficiency for the collection of samples of such a fluid.

Other objects and various advantages of the disclosed method for sampling, device for sampling, and a method of forming and assembling a device for sampling will be apparent from the following detailed description, together with the accompanying drawings, submitted for purposes of illustration only and not intended to define the scope of the invention, reference being made for that purpose to the subjoined claims.

BRIEF DESCRIPTION OF THE DRAWING

The drawing diagrammatically illustrates by way of example, not by way of limitation, one form of the invention in which:

The FIGURE is a schematic diagrammatic vertical sectional view of one fluid sampler, for example, for carrying out the disclosed method of collecting a small sample of a lighter medium floating on a heavier medium for testing or the like.

The invention disclosed herein, the scope of which being defined in the appended claims is not limited in its application to the details of construction and arrangement of parts shown and described, since the invention is capable of other embodiments and of being practiced or carried out in various other ways. Also, it is to be understood that the phraseology or terminology employed here is for the purpose of description and not of limitation. Further, many modifications and variations of the invention as hereinbefore set forth will occur to those skilled in the art. Therefore, all such modifications and variations which are within the spirit and scope of the invention herein are included and only such limitations should be imposed as are indicated in the appended claims.

DESCRIPTION OF THE INVENTIONS

This patent includes three inventions, a method for collecting a small sample of a lighter medium floating on a heavier medium for testing or the like, a mechanism for practicing the above method comprising a (1) cylindrical container for holding the two mediums, (2) a piston means with an axial opening therein operable in the cylindrical container, and an open tube means for said piston means for receiving the lighter medium from through the piston means, and (3) a method for forming and assembling a mechanism for collecting a small sample of a lighter medium floating on a heavier medium for testing or the like.

METHOD FOR COLLECTING A SMALL SAMPLE OF A LIGHTER MEDIUM

A method for collecting a small sample of a lighter medium floating on the surface of a heavier medium in an open topped container may comprise the following method step:

(1) lowering an elongated tube means 14 with a concave surface 28 on the lower end thereof down into the mediums 32 and 34 for forcing the lighter medium 32 up into the elongated tube means for testing or the like.

Or describing the method in different terms, it may comprise the following steps:

(1) lowering an elongated tube means 14 with a concave surface 28 on the lower end thereof down into the mediums 32 and 34 in the container 12, and (2) flowing the lighter medium up into the tube adjacent to the top thereof for providing a sample of the lighter medium for testing or the like.

The above first step may be described in greater detail as:

(1) slowly lowering the elongated tube with the concave shaped lower end into the container into the upper lighter medium, and heavier medium if necessary, for substantially filling the elongated tube with the lighter medium for providing the sample of the lighter medium for testing or the like.

The above second step may be defined in more detail by the following steps:

(1) flowing the lighter medium from the larger container to the smaller elongated tube, and (2) forcing the lighter medium up the elongated tube to adjacent the top thereof for providing a sample of the lighter medium for testing or the like.

The following steps may be added to the first two methods above:

(1) lowering the tube in the mediums for raising the level of the lighter medium to adjacent the top of the tube, and (2) expelling some of the heavier medium from the bottom of the container to lowering the surface of the lighter medium in the tube to the desired level.

THE PREFERRED EMBODIMENT FOR PRACTICING THE INVENTION

The above methods for collecting a small sample of a lighter medium floating on a heavier medium may be performed by other mechanisms than that disclosed in the FIGURE. The mechanism disclosed herein may be operated by other methods than those disclosed, as by hand. Also the disclosed mechanism can be used to practice another and materially different method. However, the preferred system for performing the method is disclosed in the FIGURE.

The FIGURE is a schematic diagrammatic enlarged vertical sectional view of the preferred mechanism or sampler for carrying out the above described methods. While the size may vary, the actual height of the preferred embodiment is about 14 inches (36 cm) with the diameter of the container being about 2.5 inches (6 cm).

The sampler 10 illustrated comprising basically a cylindrical container 12 and an open ended small tube 14 with an elongated lower end or piston 16 connected thereto for sliding down internally of the cylindrical container.

The cylindrical container 12 has an opening 18 in the top thereof and a base 20 attached to the bottom for a steady support. A drain pipe 22 having a manually control valve 24 is secured to the container adjacent the bottom thereof for controlled draining of the liquid from the container to a small capsule near by (not shown).

Piston 16, slidable internally of the cylindrical container 12 may utilize a sealing O-ring 26, or the like, for preventing any liquid from leaking past between the piston and the container walls. The piston has a concave or conical opening 28 in the bottom thereof opening upwardly into a cylindrical passage 30 that passes axially through the piston.

The tube 14 is secured tightly internally of the piston as with a suitable cement for allowing free passage of lighter fluid 32 from the container up through the piston to the top of the open tube with the heavier fluid 34 below in the container 12. The tube 14 need be only large enough to receive a hydrometer 36 as illustrated.

A weight 38, as in the form of a brass annulus is positioned around the tube 14 for resting on the piston 16 and secured thereto, if desired, for balancing the oil column in the tube.

Briefly, in operation of the sampler 10, the two fluids are poured into the cylindrical container and after the lighter fluid 32 has risen to the top of the heavier fluid 54, the tube 14 with enlarged lower end or piston 16 is slowly lowered into the cylindrical container 12 for forcing the lighter fluid 32 up through the piston to substantially fill the small tube. Then the sample of lighter fluid, as in our case floating on the heavier fluid as water, is ready for testing, as by either inserting a hydrometer therein as illustrated, by taking a sample thereof with a syringe for testing, or using other means of testing of the lighter fluid.

METHOD FOR FORMING AND ASSEMBLING A SAMPLER

The above mechanism for collecting a small sample of a lighter medium floating on the surface of a heavier medium may be assembled by various methods. However, the preferred method for assembling the mechanism, as sampling mechanism 10 in the drawing may comprise the following method steps:

(1) forming an upright cylindrical open ended container by machining a large tube of Plexiglas to the desired shape and size for eventually holding the lighter and heavier mediums, and (2) slidably mounting an elongated tube machined from a tube of Plexiglas with an enlarged lower end in the cylindrical container open end for being submerged in the mediums for forcing the lighter medium to the top of the elongated tube resulting in a sampler for providing a sample of the lighter medium floating on the heavier medium for testing or the like. This enlarged end is formed from a block of Plexiglas being machined to shape to slide in the machined cylindrical container.

By expanding into more details, the method may be expressed thus:

(1) forming an upright cylindrical open ended container for eventually being at least partially filled with the lighter and heavier mediums, (2) securing an enlongated tube machined from a tube of Plexiglas to the top of an axial opening drilled through a piston, and (3) slidably mounting the piston on the upper open end of the cylindrical container for being submerged in the mediums for forcing the lighter medium to the top of the elongated tube resulting in a sampler for providing a sample of the lighter medium floating on the heavier medium for testing or the like.

The above basic method may include the following steps:

(4) forming the piston with an inverted cone shaped entrance to its axial opening tapering from substantially the diameter of the piston bottom to the diameter of the elongated tube for funneling the lighter medium up to the top of the elongated tube as the piston is lowered in the two mediums. The inverted cone shape is formed in the bottom of the piston by machining the inverted cone shape in a block of Plexiglas as illustrated in the drawing. The Plexiglas piston is cemented to the elongated small Plexiglas tube after the axial hole is machined in the piston.

The above basic method also may include the following step instead:

(4) securing a brass annular weight means to the tube as by cementing the annular weight to either the tube or the piston for balancing the lighter medium in the elongated tube.

Obviously other methods may be utilized for collecting a small sample of a lighter medium floating on the surface of a heavier medium shown in the FIGURE than those listed above, depending on the particular type of samples desired.

Accordingly, it will be seen that while only one sampling mechanism is disclosed in the drawing and described above, it will operate in a manner which meets each of the objects set forth hereinbefore.

While only two methods of the invention and one mechanism for carrying out one of the methods have been disclosed, it will be evident that various other methods and modifications are possible in the arrangement and construction of the disclosed methods and sampling mechanism without departing from the scope of the invention and it is accordingly desired to comprehend within the purview of this invention such modifications as may be considered to fall within the scope of the appended claims.

I claim:

1. A method for collecting a small sample of a lighter medium floating on the surface of a heavier medium in an open topped container comprising the method steps of:
    (a) lowering an elongated tube means with a concave surface on the lower end thereof down into the mediums for forcing the lighter medium up into the elongated tube means, and
    (b) balancing the column or light medium up in the open topped container with weight means for the elongated tube means for testing or the like.

2. A method for collecting a small sample of a lighter medium floating on the surface of a heavier medium in an open topped container comprising the method steps of:
    (a) submerging an elongated tube with a close fitting enlarged lower end into the container with the mediums therein for forcing the lighter medium to the top of the elongated tube for providing a sample of the lighter medium, and
    (b) balancing the lighter medium at the top of the elongated tube with an annular weight means mounted around the elongated tube for testing or the like.

3. A method for collecting a small sample of a lighter medium floating on the surface of a heavier medium in an open topped container comprising the steps of:
    (a) lowering an elongated tube with a concave surface on the lower end thereof down into the lighter medium in the container, and
    (b) flowing and balancing the lighter medium up into the tube to adjacent the top thereof with weight means for the elongated tube for providing a sample of the lighter medium for testing or the like.

4. A method as recited in claim 3 wherein the first method step comprises further:
    (a) slowly lowering the elongated tube with the concave shaped lower end into the container into the upper lighter medium, and heavier medium if necessary, for substantially filling the elongated tube with the lighter medium for providing the sample of the lighter medium for testing or the like.

5. A method as recited in claim 3 wherein the second method step comprises further:
    (a) flowing the lighter medium from the larger container to the smaller elongated tube, and
    (b) forcing and balancing the lighter medium up the elongated tube to adjacent the top thereof with weight means mounted around the elongated tube for providing a sample of the lighter medium for testing or the like.

6. A method as recited in claim 3 wherein the second method step comprises further,
    (a) lowering the tube in the mediums for rasing the level of the lighter medium to adjacent the top of the tube, and
    (b) controlling and expelling some of the heavier medium from the bottom of the container with valve means downstream of the container for lowering the surface of the lighter medium in the tube to the desired level.

7. A sampling mechanism for collecting a small sample of a lighter medium floating on the surface of a heavier medium in the bottom of the device comprising,
    (a) a cylindrical container means for holding the two mediums,
    (b) an elongated tube means having a concave lower surface slidable in said cylindrical container down into the mediums for forcing the lighter medium up into the elongated tube means for testing or the like, and
    (c) said elongated tube means having weight means for balancing the column of light medium is said tube means.

8. A sampling mechanism for collecting a small sample of a lighter medium floating on the surface of a heavier medium in the bottom of the device comprising,
    (a) open topped cylindrical container means for holding the two mediums,
    (b) an elongated tube means having an enlarged lower end for closely fitting into the open topped cylindrical container means with the mediums therein for forcing the lighter medium to the top of the elongated tube, and
    (c) said elongated tube means has weight means for balancing the column of light medium in said tube means for providing a sample of the lighter medium for testing or the like.

9. A sampling mechanism for collecting a small sample of a lighter medium floating on the surface of a heavier medium comprising,
    (a) cylindrical container means for holding the two mediums,
    (b) piston means with an axial opening therein operable in the cylindrical container means and positionable on the upper surface of the lighter medium, and
    (c) open tube means for said piston means for receiving the lighter medium from through the piston means axial opening as said piston means is lowered in said cylindrical container until the lighter medium fills the upper portion of said open tube means, and
    (d) an annular weight means mounted around said open tube means for balancing and forcing the column of light medium to the top of said open tube means for providing a sample of the lighter medium for testing or the like.

10. A sampling mechanism for collecting a small sample of a lighter medium floating on the surface of a heavier medium comprising,
    (a) cylindrical container means for holding the two mediums,
    (b) piston means with an axial opening therein operable in the cylindrical container and positionable on the upper surface of the lighter medium,
    (c) said piston means has weight means for balancing the column of light medium in an open tube means, and
    (d) said open tube means for said piston means receives the lighter medium from through the piston means axial opening as said piston means is lowered in said cylindrical container until the lighter medium fills the upper portion of said open tube means for providing a sample of the lighter medium for testing or the like.

11. A sampling mechanism for collecting a small sample of a light medium floating on the surface of a heavier medium comprising,
   (a) cylindrical container means for holding the two mediums,
   (b) piston means with an axial opening therein operable in the cylindrical container and positionable on the upper surface of the lighter medium,
   (c) said piston means has weight means for balancing the column of light medium in said tube means,
   (d) open tube means for said piston means for receiving the lighter medium from through the piston means axial opening as said piston means is lowered in said cylindrical container until the lighter medium fills the upper portion of said open tube means for providing a sample of the lighter medium for testing or the like, and
   (e) said weight means being an annular weight means mounted around said open tube means for balancing and forcing the column of light medium to the top of said open tube means.

12. A sampling mechanism for collecting a small sample of a lighter medium floating on the surface of a heavier medium in the bottom of the device comprising,
   (a) open topped cylindrical container means for holding the two mediums,
   (b) an elongated tube means having an enlarged lower end for closely fitting into the open topped cylindrical container means with the mediums therein for forcing the lighter medium to the top of said elongated tube means, and
   (c) piston means for said elongated tube means having an inverted cone shaped entrance to its axial opening tapering from substantially the diameter of the piston bottom to the diameter of said elongated tube means for funneling the lighter medium up said elongated tube means as said piston is lowered in the two mediums for providing a sample of the lighter medium for testing or the like.

13. A sampling mechanism for collecting a small sample of a lighter medium floating on the surface of a heavier medium in the bottom of the device comprising,
   (a) open topped cylindrical container means for holding the two mediums,
   (b) an elongated tube means having an enlarged lower end for closely fitting into the open topped cylindrical container means with the mediums therein for forcing the lighter medium to the top of said elongated tube means, and
   (c) piston means for said elongated tube means having an inverted cone shaped entrance to its axial opening tapering from substantially the diameter of the piston bottom to the diameter of said elongated tube means as said piston is lowered in the two mediums for providing a sample of the lighter medium for testing or the like,
   (d) said cylindrical container has a valve at the bottom thereof for expelling a desired amount of the heavier medium for adjusting the height of the lighter medium in said open end tube means, and
   (e) said piston means having sealing O-rings therearound for preventing passage of the liquids past the piston means to the upper portion of said cylindrical container.

14. A method for forming and assembling a sampler for collecting a small sample of a lighter medium floating on the surface of a heavier medium comprising the steps of
   (a) forming an upright open ended cylindrical container for holding the lighter and heavier mediums,
   (b) slideably mounting an elongated tube with an enlarged lower end in the cylindrical container open end for being submerged in the mediums for forcing the lighter medium to the top of the elongated tube, and
   (c) positioning a weight means on the elongated tube for balancing the light medium in the elongated tube resulting in a sampler for providing a sample of the lighter medium floating on the heavier medium for testing or the like.

15. A method for forming and assembling a sampler for collecting a small sample of a lighter medium floating on the surface of a heavier medium comprising the steps of,
   (a) forming an upright cylindrical open ended container for being at least partially filled with the lighter and heavier mediums,
   (b) securing an elongated tube to the top of an axial opening through a piston,
   (c) mounting an annular weight means around the elongated tube for balancing and forcing the column of light medium to the top of the elongated tube, and
   (d) slidably mounting the piston in the upper open end of the cylindrical container for being submerged in the mediums for forcing the lighter medium to the top of the elongated tube resulting in a sampler for providing a sample of the lighter medium floating on the heavier medium for testing or the like.

16. A method for forming and assembling a sampler for collecting a small sample of a lighter medium floating on the surface of a heavier medium comprising the steps of,
   (a) forming an upright open ended cylindrical container for holding the lighter and heavier mediums, and
   (b) slidably mounting an elongated tube with an enlarged lower end in the cylindrical container open end for being submerged in the mediums for forcing the lighter medium to the top of the elongated tube,
   (c) attaching a piston to the lower end of the elongated tube, and
   (d) forming the bottom of the piston to a concave shape for funneling the lighter medium up through the piston to the top of the elongated tube, resulting in a sampler for providing a sample of the lighter medium floating on the heavier medium for testing or the like.

17. A method for forming and assembling a sampler for collecting a small sample of a lighter medium floating on the surface of a heavier medium comprising the steps of,
   (a) forming an upright cylindrical open ended container for being at least partially filled with the lighter and heavier mediums,
   (b) securing an elongated tube to the top of an axial opening through a piston,
   (c) slidably mounting the piston in the upper open end of the cylindrical container for being submerged in the mediums for forcing the lighter medium to the top of the elongated tube and, (d) forming the piston with an inverted cone shaped entrance to its axial opening tapering from substantially the diameter of the piston bottom to the diameter of the elongated tube for funneling the lighter medium up to the top of the elongated tube as the piston is lowered in the two mediums resulting in a sampler for providing a sample of the lighter medium floating on the heavier medium for testing or the like.

18. A method for forming and assembling a sampler for collecting a small sample of a lighter medium floating on the surface of a heavier medium comprising the steps of,
   (a) forming an upright open ended cylindrical container for holding the lighter and heavier mediums,
   (b) slidably mounting an elongated tube with an enlarged lower end in the cylindrical container open end for being submerged in the mediums for forcing the lighter medium to the top of the elongated tube, and
   (c) securing a weight means to the tube and piston combination for balancing the lighter medium in the elongated tube resulting in a sampler for providing a sample of the lighter medium floating on the heavier medium for testing or the like.

19. A method for forming and assembling a sampler for collecting a small sample of a lighter medium floating on the surface of a heavier medium comprising the steps of,
   (a) forming an upright cylindrical open ended container for being at least partially filled with the lighter and heavier mediums,
   (b) securing an elongated tube to the top of an axial opening through a piston,
   (c) slidably mounting the piston in the upper open end of the cylindrical container for being submerged in the mediums for forcing the lighter medium to the top of the elongated tube, and
   (d) mounting an annular weight on the piston around the elongated tube for balancing the lighter medium in the elongated tube resulting in a sampler for providing a sample of the lighter medium floating on the heavier medium for testing or the like.

20. A sampling mechanism for collecting a small sample of a lighter medium floating on the surface of a heavier medium comprising,
   (a) cylindrical container means for holding the two mediums,
   (b) piston means with an axial opening therein operable in the cylindrical container and positionable on the upper surface of the lighter medium,
   (c) open tube means for said piston means for receiving the lighter medium from through the piston means axial opening as said piston means is lowered in said cylindrical container until the lighter medium fills the upper portion of said open tube means, and
   (d) said piston means has an inverted cone shaped entrance to its axial opening tapering from substantially the diameter of the piston bottom to the diameter of said open tube means for funneling the lighter medium up said open tube means as said piston is lowered in the two mediums for providing a sample of the lighter medium for testing or the like.

21. A sampling mechanism for collecting a small sample of a lighter medium floating on the surface of a heavier medium comprising,
   (a) cylindrical container means for holding the two mediums,
   (b) piston means with an axial opening therein operable in the cylindrical container and positionable on the upper surface of the lighter medium,
   (c) said piston means has weight means for balancing the column of light medium in said tube means,
   (d) open tube means for said piston means for receiving the lighter medium from through the piston means axial opening as said piston means is lowered in said cylindrical container until the lighter medium fills the upper portion of said open tube means, and
   (e) said piston means has an inverted cone shaped entrance to its axial opening tapering from substantially the diameter of the piston bottom to the diameter of said open tube means for funneling the lighter medium up said open tube means as said piston is lowered in the two mediums for providing a sample of the lighter medium for testing or the like.

22. A sampling mechanism for collecting a small sample of a lighter medium floating on the surface of a heavier medium comprising,
   (a) cylindrical container means for holding the two mediums,
   (b) piston means with an axial opening therein operable in the cylindrical container and positionable on the upper surface of the lighter medium,
   (c) open tube means for said piston means for receiving the lighter medium from through the piston means axial opening as said piston means is lowered in said cylindrical container until the lighter medium fills the upper portion of said open tube means for providing a sample of the lighter medium for testing or the like,
   (d) said piston means has an inverted cone shaped entrance to its axial opening tapering from substantially the diameter of the piston bottom to the diameter of said open tube means for funneling the lighter medium up said open tube means as said piston is lowered in the two mediums,
   (e) said cylindrical container has a valve at the bottom thereof for expelling a desired amount of the heavier medium for adjusting the height of the lighter medium in said open end tube means, and
   (f) said piston means having sealing O-rings therearound for preventing passage of the liquids past the piston to the upper portion of said cylindrical container.

23. A sampling mechanism for collecting a small sample of a lighter medium floating on the surface of a heavier medium comprising,
   (a) cylindrical container means for holding the two mediums,
   (b) piston means with an axial opening therein operable in the cylindrical container and positionable on the upper surface of the lighter medium,
   (c) said piston means has weight means for balancing the column of light medium in said tube means,
   (d) open tube means for said piston means for receiving the lighter medium from through the piston means axial opening as said piston means is lowered in said cylindrical container until the lighter medium fills the upper position of said open tube means,
   (e) said piston means has an inverted cone shaped entrance to its axial opening tapering from substantially the diameter of the piston bottom to the diameter of said open tube means for funneling the lighter medium up said open tube means as said piston is lowered in the two mediums, (f) said cylindrical container has a valve at the bottom thereof for expelling a desired amount of the heavier medium for adjusting the height of the lighter medium in said open end tube means, and (g) said piston means having sealing O-rings therearound for preventing passage of the liquids past the piston means to the upper portion of said cylindrical container.

24. A method for forming and assembling a sampler for collecting a small sample of a lighter medium floating on the surface of a heavier medium comprising the steps of, (a) forming an upright cylindrical open ended container for being at least partially filled with the lighter and heavier mediums, (b) securing an elongated tube to the top of an axial opening through a piston, (c) slidably mounting the piston in the upper open end of the cylindrical container for being submerged in the mediums for forcing the lighter medium to the top of the elongated tube, and (d) forming the bottom of the piston to a concave shape for funneling the lighter medium up through the piston to the top of the elongated tube resulting in a sampler for providing a sample of the lighter medium floating on the heavier medium for testing or the like.

25. A method for forming and assembling a sampler for collecting a small sample of a lighter medium floating on the surface of a heavier medium comprising the steps of, (a) forming an upright open ended cylindrical container for holding the lighter and heavier mediums, (b) slidably mounting an elongated tube with a piston on the lower end in the cylindrical container open end for being submerged in the mediums for forcing the lighter medium to the top of the elongated tube, and (c) forming the piston with a concave bottom and an inverted cone shaped entrance to its axial opening tapering from substantially the diameter of the piston bottom to the diameter of the elongated tube for funneling the lighter medium up to the top of the elongated tube as the piston is lowered in the two mediums, resulting in a sampler for providing a sample of the lighter medium floating on the heavier medium for testing or the like.

26. A method for forming and assembling a sampler for collecting a small sample of a lighter medium floating on the surface of a heavier medium comprising the steps of, (a) forming an upright cylindrical open ended container for being at least partially filled with the lighter and heavier mediums, (b) securing an elongated tube to the top of an axial opening through a piston, (c) slidably mounting the piston in the upper open end of the cylindrical container for being submerged in the mediums for forcing the lighter medium to the top of the elongated tube, (d) forming the bottom of the piston to a concave shape for funneling the lighter medium up through the piston to the top of the elongated tube, (e) forming the piston with an inverted cone shaped entrance to its axial opening tapering from substantially the diameter of the piston bottom to the diameter of the elongated tube for funneling the lighter medium up to the top of the elongated tube as the piston is lowered in the two mediums resulting in a sampler for providing a sample of the lighter medium floating on the heavier medium for testing or the like.

27. A method for forming and assembling a sampler for collecting a small sample of a lighter medium floating on the surface of a heavier medium comprising the steps of, (a) forming an upright cylindrical open ended container for being at least partially filled with the lighter and heavier mediums, (b) securing an elongated tube to the top of an axial opening through a piston, (c) slidably mounting the piston in the upper open end of the cylindrical container for being submerged in the mediums for forcing the lighter medium to the top of the elongated tube, and (d) securing a weight means to the tube and piston combination for balancing the lighter medium in the elongated tube resulting in a sampler for providing a sample of the lighter medium floating on the heavier medium for testing or the like.

* * * * *